(12) United States Patent
Bieser et al.

(10) Patent No.: US 9,272,975 B2
(45) Date of Patent: *Mar. 1, 2016

(54) CONTINUOUS PROCESS FOR THE PRODUCTION OF DERIVATIVES OF SATURATED CARBOXYLIC ACIDS

(71) Applicant: Novamont S.p.A., Novara (IT)

(72) Inventors: Arno Bieser, Weinheim (DE); Giampietro Borsotti, Novara (IT); Francesca Digioia, Barengo (IT); Adriano Ferrari, Trescore Balneario (IT); Alessandro Pirocco, Cameri (IT)

(73) Assignee: Novamont S.p.A., Novara (IT)

(*) Notice: Subject to any disclaimer, the term of this patent is extended or adjusted under 35 U.S.C. 154(b) by 0 days.

This patent is subject to a terminal disclaimer.

(21) Appl. No.: 14/468,809

(22) Filed: Aug. 26, 2014

(65) Prior Publication Data

US 2015/0073162 A1  Mar. 12, 2015

Related U.S. Application Data

(63) Continuation of application No. 13/520,042, filed as application No. PCT/EP2010/070844 on Dec. 29, 2010, now Pat. No. 8,846,962.

(30) Foreign Application Priority Data

Dec. 30, 2009 (IT) .............................. MI2009A2361

(51) Int. Cl.
  *C07C 33/00* (2006.01)
  *C07C 51/353* (2006.01)
  *C07C 51/245* (2006.01)
  *C07C 51/44* (2006.01)

(52) U.S. Cl.
  CPC ............. *C07C 51/353* (2013.01); *C07C 51/245* (2013.01); *C07C 51/44* (2013.01)

(58) Field of Classification Search
  CPC ...... C07C 51/44; C07C 51/245; C07C 51/353
  USPC ........................................................... 554/138
  See application file for complete search history.

(56) References Cited

U.S. PATENT DOCUMENTS 4,606,863 A  8/1986  Nakazawa et al.

FOREIGN PATENT DOCUMENTS

| WO | WO-94/10122 A1 | 5/1994 |
| WO | WO-2007/039481 A1 | 4/2007 |
| WO | WO-2008/138892 A1 | 11/2008 |
| WO | WO 2008138892 A1 * | 11/2008 |

* cited by examiner

*Primary Examiner* — Deborah D Carr
(74) *Attorney, Agent, or Firm* — Novak Druce Connolly Bove + Quigg LLP

(57) ABSTRACT

Provided is a continuous process for the oxidative cleavage of derivatives of unsaturated carboxylic acids for the production of saturated carboxylic acids and their derivatives which comprises the steps of:
a) feeding to a first reactor at least a derivative of an unsaturated carboxylic acid, an oxidizing compound and a catalyst capable of catalyzing the oxidation reaction of the olefinic double bond to obtain an intermediate compound containing vicinal diols, and of
b) feeding to a second reactor said intermediate compound, a compound containing oxygen and a catalyst capable of catalyzing the oxidation reaction of the vicinal diols to carboxylic groups, to obtain saturated monocarboxylic acids (i) and derivatives of saturated carboxylic acids with more than one acid function (ii);
c) separating the saturated monocarboxylic acids (i) from the derivatives of carboxylic acids having more than one acid function (ii).

23 Claims, 4 Drawing Sheets

The flow diagram of the process according to the invention

FIG. 1: The flow diagram of the process according to the invention

FIG. 2: A diagram of the plant in which the process takes place

FIG. 3: Hydrogen peroxide concentration in the reaction mixture during step a) of the Example 1 (continuous process according to the invention with a $H_2O_2$ starting concentration of 60%);

FIG. 4: The time-course concentration of hydrogen peroxide during step a) of Example 2 Comparative (batch process with a $H_2O_2$ starting concentration of 60%).

FIG. 5: The time-course concentration of hydrogen peroxide during step a) of Example 3 Comparative (batch process with a $H_2O_2$ starting concentration of 50%).

CONTINUOUS PROCESS FOR THE PRODUCTION OF DERIVATIVES OF SATURATED CARBOXYLIC ACIDS

CROSS REFERENCE TO RELATED APPLICATIONS

This application is a Continuation of co-pending U.S. application Ser. No. 13/520,042 filed on Jun. 29, 2012, which is a National Phase filing of PCT/EP2010/070844 filed on Dec. 29, 2010; and this application claims priority to Application No. MI2009A002361 filed in Italy on Dec. 30, 2009. The entire contents of each application is hereby incorporated by reference in its entirety.

DESCRIPTION

The present invention relates to a continuous process for the oxidative cleavage of derivatives of unsaturated carboxylic acids for the production of saturated carboxylic acids and their derivatives comprising the steps of:
a) feeding to a first reactor at least a derivative of an unsaturated carboxylic acid, an oxidizing compound and a catalyst capable of catalyzing the oxidation reaction of the olefinic double bond to obtain an intermediate compound containing vicinal diols, and of
b) feeding to a second reactor said intermediate compound, a compound containing oxygen and a catalyst capable of catalyzing the oxidation reaction of the vicinal diols to carboxylic groups, to obtain saturated monocarboxylic acids (i) and derivatives of saturated carboxylic acids with more than one acid function (ii);
c) separating the saturated monocarboxylic acids (i) from the derivatives of carboxylic acids having more than one acid function (ii).

Processes for the production of saturated carboxylic acids and their derivatives are known in the literature.

For example, the patent application WO2007/039481 describes a batch process for the production of derivatives of saturated carboxylic acids characterized in that the oxidation reactions are performed on derivatives of unsaturated carboxylic acids, without the addition of organic solvents and in the presence of limited quantities of water (water:diol <1:1).

The oxidation reactions described are significantly exothermic and require constant control, together with adequate removal of the heat developed in order to prevent an excessive increase of the temperature.

The oxidation phase of the unsaturated carbons to form vicinal diols, in particular, is subject to the risk of explosive decomposition of the peroxide used as oxidizing agent, as peroxide is very unstable in conditions of high temperature.

Moreover, a further limit of the entire process is related to the accidental accumulation of oxidizing agent, which can cause sudden acceleration of the reaction with consequent uncontrolled increase of the temperature. Such accumulation can depend on a low reaction velocity or on difficulty in the mixing of oxidizing agents with reagents.

In the oxidative cleavage step of the vicinal diols, for example, significant difficulties are encountered in mixing, as at the conditions used the reagents form a liquid phase characterized by high viscosity, while the oxidizing agent is in gaseous phase.

Furthermore, the mechanism of the oxidative cleavage reaction of the vicinal diols with oxygen has been demonstrated to be of radical type. Such type of reaction shows an induction time in which the appropriate radicals concentration has to be reached before starting the reaction; after this time the reaction starts propagating exponentially and uncontrolled, with the formation of by-products having different chain length due to lack of selectivity.

To overcome the aforesaid drawbacks, the present continuous process for the production of saturated carboxylic acids and their derivatives has been developed. In said process, each of the oxidation reactions is conducted continuously and not in a batch process.

The term continuous is intended as a process in which the operations to feed reagents and to remove products take place simultaneously for the entire duration thereof and in which, in each step, the process conditions (i.e. temperature, pressure, flow rate, etc.) remain substantially unchanged.

The continuous process according to the present invention is more effectively controllable with respect to known processes, making it possible to feed high concentrations of oxidizing agent in safe conditions during step a) of the process.

Moreover, the continuous process according to the invention solves the difficulties of mixing the oxidizing agent during the oxidative cleavage reaction of the diols, linked to the high viscosity of the reaction mixture. In fact, in said process for the entire duration of step b) the reaction mixture contains a high percentage of reaction products which, being more fluid than the reagents, contribute towards significantly decreasing the viscosity of the system.

In the continuous process according to the invention it is also possible to maintain constant and low the radicals concentration during step b), thus limiting the formation of by-products and increasing the reaction yield.

The process according to the invention will now be described in greater detail with reference to the accompanying figures, wherein.

Figure 1:
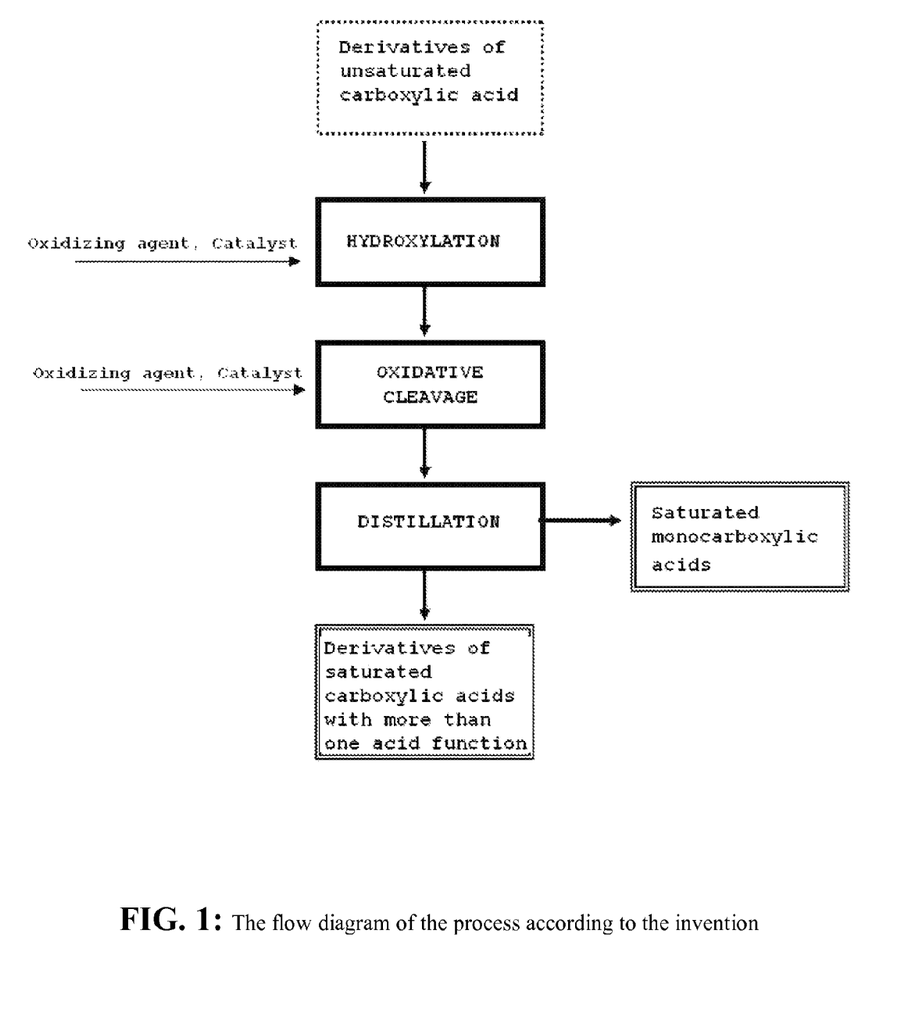
FIG. 1 is a flow diagram of the process according to the invention.
Figure 2:
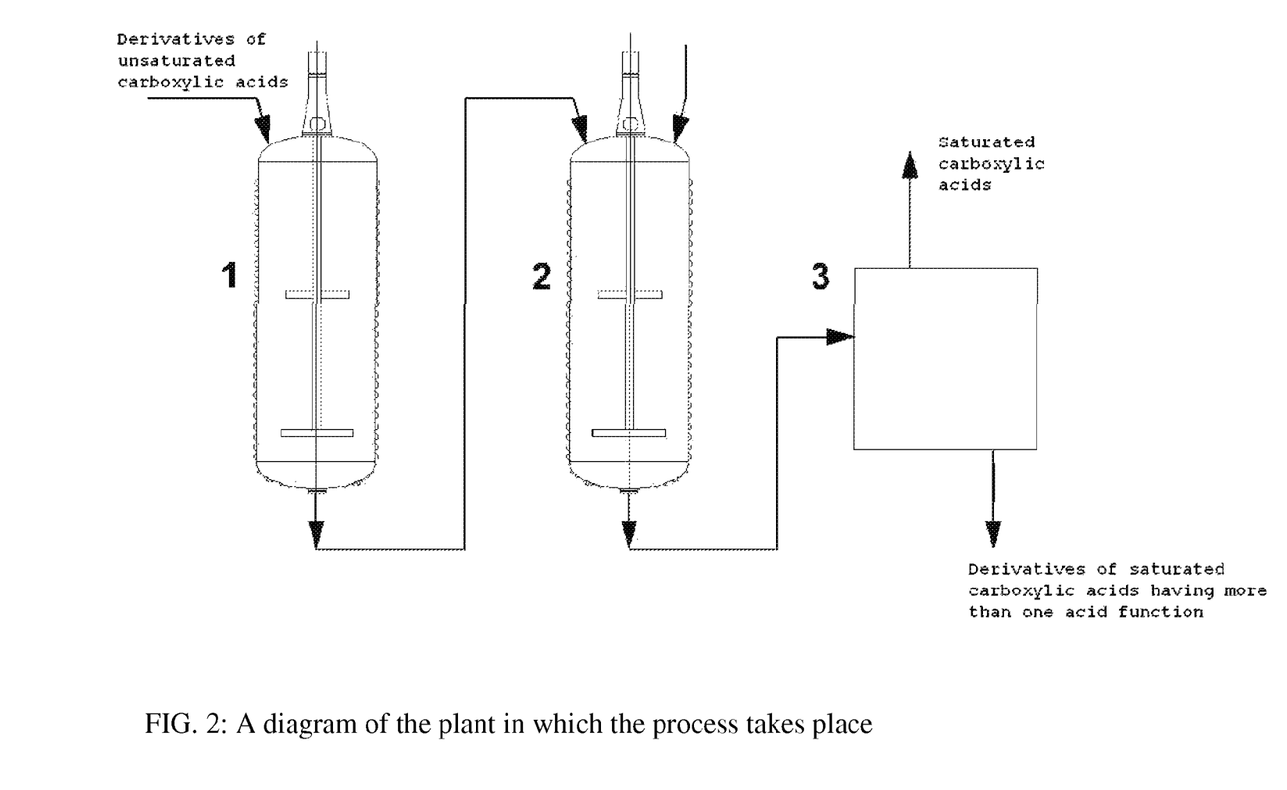
FIG. 2 is a diagram of the plant in which the process takes place.

The present invention relates in particular to a continuous process for the oxidative cleavage of derivatives of unsaturated carboxylic acids for the production of saturated carboxylic acids and their derivatives, comprising the steps of:
a) feeding to a first continuous reactor (1) at least a derivative of an unsaturated carboxylic acid, an oxidizing compound and a catalyst capable of catalyzing the oxidation reaction of the olefinic double bond to obtain an intermediate compound containing vicinal diols, and of
b) feeding to a second continuous reactor (2) said intermediate compound, oxygen or a compound containing oxygen and a catalyst capable of catalyzing the oxidation reaction of the vicinal diols to carboxylic groups, to obtain saturated monocarboxylic acids (i) and derivatives of saturated carboxylic acids with more than one acid function (ii);

c) transferring the product of step b) to an apparatus suitable to separate the saturated monocarboxylic acids (i) from the derivatives of carboxylic acids having more than one acid function (ii).

The starting material for the process according to the present invention is a derivative of an unsaturated carboxylic acid. With the term "derivative of an unsaturated carboxylic acid" is meant a carboxylic acid in which the carboxylic group is reacted so as to prevent or minimize any further reactions of this carboxylic group thus modified in the course of the process.

The unsaturated carboxylic acid can be either monounsaturated or polyunsaturated. Example of unsaturated carboxylic acids are: 9-tetradecenoic acid (myristoleic acid), 9-hexadecenoic acid (palmitoleic acid), 9-octadeceneoic acid (oleic acid), 12-hydroxy-9-octadeceneoic acid (ricinoleic acid), 9-eicosenoic acid (gadoleic acid), 13-docosenoic acid (erucic acid), 15-tetracosenoic acid (nervonic acid), 9,12-octadecadienoic acid (linoleic acid), and 9,12,15-octadecatrienoic acid (linolenic acid).

Mixtures of the derivatives of unsaturated carboxylic acids can also be used. Mixtures of unsaturated carboxylic acids, for example, are those present in vegetable oils such as soybean oil, olive oil, castor oil, sunflower oil, peanut oil, maize oil, palm oil, jatropha oil, cuphea oil, oils from Brassicaceae such as *Crambe abyssinica, Brassica carinata, Brassica napus* (rapeseed), *Lesquerella*, and other oils with a high monounsaturated acid content.

Monounsaturated carboxylic acids are particularly preferred. The use of oleic acid and of erucic acid is particularly advantageous in the process according to the invention. In these cases pelargonic acid with high yields is obtained as saturated monocarboxylic acid.

Derivatives of carboxylic acids can be obtained by reacting the carboxylic group with an alcohol (i.e. ester), an amine (i.e. amide, nitrile), a thiol (i.e. thioester) etc. In the case of reaction with an alcohol, the esters obtained preferably comprise the C1-C9 alkyl groups, more preferably the methyl, ethyl and propyl groups.

The use of methyl and ethyl esters is particularly advantageous, in particular those obtained by transesterification of methanol and ethanol with the triglycerides contained in sunflower oil with a high oleic acid content and/or in oils from Brassicaceae with a high erucic acid content.

In the process according to the invention the reactors 1 and 2 used to perform steps a) and b), are continuous reactors, preferably connected each other by means of a gear pump. The use of these continuous reactors allows a reduction of the reaction volumes, facilitating heat exchange.

In a preferred embodiment of the process, the reactors 1 and 2 are of the CSTR (Continuous Stirred-Tank Reactor) type. Each of the CSTRs 1 and 2 can advantageously be substituted by several reactors of the same type arranged in series, determining an increase in the surface/volume ratio (consequently further facilitating heat exchange during the reaction) and the reduction of the total reaction volume.

In step b) continuous reactors of gas/liquid type are advantageously used. Preferably, jet loop reactors (CSTR Loop), which promote contact between the oxidizing agent in gaseous phase and the reaction mixture in liquid phase, are used.

Both steps a) and b) are preferably conducted without the addition of organic solvents.

In a preferred embodiment of the process, step b) is conducted without the addition of water besides that in which the catalyst is dissolved. Advantageously, during said step b) the aqueous phase/organic phase ratio is maintained below 1:3 by weight.

The oxidizing substance used to perform step a) of the process according to the invention is preferably selected from osmium tetroxide, permanganates, hydrogen peroxide, alkyl hydroperoxides and percarboxylic acids as, for example, performic acid, peracetic acid or perbenzoic acids. Said oxidizing substance is more preferably an aqueous solution of hydrogen peroxide in concentrations between 30 and 80%, preferably between 40 and 70% and even more preferably between 49 and 65%.

In the continuous process according to the present invention it is possible to use solutions of hydrogen peroxide even at very high concentrations. In fact, the continuous nature of the process allows the concentration of peroxide to be kept constant during the reaction, preventing dangerous phenomena of accumulation thereof which can instead occur during batch type reactions. Surprisingly, the applicant has found that the $H_2O_2$ concentration during the continuous process according to the invention is even lower than the one observed during a batch process performed with lower starting concentration of hydrogen peroxide.

The use of hydrogen peroxide solutions at high concentrations has the advantage of introducing lower quantities of dilution water into the reaction mixture.

The diol resulting from step a) is continuously fed, preferably by a gear pump, to reactor 2, where it is allowed to react—in step b)—with oxygen or with a compound containing oxygen. The use of air is particularly advantageous. Oxygen enriched air can also be used.

The catalyst of step a) belongs to the group of transition elements. Advantageously, Fe, Mn, Mo, Nb, Os, Re, Ti, V, W, Zr and their acids, alkaline salts and complexes are used as catalysts in homogeneous or heterogeneous phase, optionally in a supported or nanostructured form. The use of tungstic acid or phosphotungstic acid is particularly preferred. Said catalyst is present in quantities between 0.03% and 3% by moles, preferably between 0.05% and 1.8% by moles and even more preferably between 0.06% and 1.5% by moles with respect to the total moles of unsaturations. In a preferred embodiment of the process, the catalyst can be fed in solution form in a non-organic solvent.

With regard to the catalyst of step b), it belongs to the group of the transition elements. Advantageously, Ce, Cr, Co, Cu, Mn, Mo, Re, Os, V and W and their acids, alkaline salts and complexes are used as catalysts in homogeneous or heterogeneous phase, optionally in a supported or nanostructured form. The use of cobalt salts such as acetate, chloride, sulphate, bromide and nitrate, used in quantities between 0.05% and 3% by moles, preferably between 0.1% and 2% by moles and even more preferably between 0.3% and 1.5% by moles with respect to the diol produced in step a) is particularly preferred. The use of cobalt acetate and of cobalt chloride is particularly preferred.

An inorganic acid can be added to the catalyst of step b). Examples of inorganic acid are phosphoric acid, sulphuric acid, hydrochloric acid, perchloric acid and mixtures thereof.

The startup phase of the continuous process according to the invention can be carried out by adding a small quantity of the intermediate compound obtained with step a), as the diols contained therein promote activation of the reaction. Said intermediate compound can be added in a quantity ≤5%, preferably ≤3% in weight with respect to the starting oil.

Advantageously, during step a) of the process according to the invention, nitrogen or air are made to flow to remove a part of the water produced in the process. In this manner excessive dilution of $H_2O_2$ of is avoided. An alternative to the flow of these gases is vacuum evaporation.

The reaction temperature of step a) and of step b) of the present process is advantageously between 45 and 95° C., preferably between 50 and 90° C.

The reaction temperature of phase (a) is advantageously between 55 and 80° C.

The reaction temperature of step b) is advantageously between 55 and 90° C. and even more advantageously between 60 and 70° C.

Advantageously, to perform both step a) and step b) of the present process, the average retention time in the reactor is between 2 and 8 hours.

In a preferred embodiment of the process, the intermediate product resulting from step a) is fed directly to the reactor in which step b) is performed. In fact, it has surprisingly been found that by feeding the intermediate product directly to the oxidative cleavage reactor, this reaction time is decreased with respect to batch reaction, due to the greater reactivity of this intermediate product. This increase in reactivity also determines a significant increase in the reaction yield.

The process according to the invention can be advantageously performed at atmospheric pressure or in any case at moderate partial oxygen pressures therefore resulting particularly advantageous in terms of industrial production.

Step a) is preferably performed at atmospheric pressure or at a pressure slightly below atmospheric pressure.

Step b) is preferably performed with air at a pressure of $\leq 50 \cdot 10^5$ Pa, preferably $\leq 25 \cdot 10^5$ Pa. In a preferred embodiment of the process according to the invention, at the end of step a) the catalyst can be removed from the reaction mixture and recovered by known techniques.

Advantageously, the aqueous phase of the product obtained as output from step b) is separated from the organic phase.

Organic phase separation can be advantageously performed by continuous centrifuging by means of a disc separator or with other established separation techniques.

Optionally a small amount of organic solvent can be added to improve the separation of the two phases.

The aqueous phase contains the catalyst of step b) and, if it has not been removed, also the catalyst of step a). These catalysts can be recovered and optionally recycled as catalysts of step b). The organic phase is a clear oil consisting of a mixture substantially comprising saturated monocarboxylic acids and derivatives of saturated carboxylic acids having more than one acid function, derivatives of saturated monocarboxylic acids present in the starting mixture and of the vicinal diol formed during step a), comprising a reaction residue consisting of esters of the diol with saturated carboxylic acids having one or more acid functions.

In a preferred embodiment of the process, in which methyl esters of carboxylic acids obtained by transesterification of sunflower oil are used as starting material, the organic phase is substantially composed of pelargonic acid and mono-methyl azelate, methyl palmitate, methyl stearate and methyl dihydroxy stearate, this latter in free form or esterified with pelargonic acid and/or mono-methyl azelate.

In another preferred embodiment of the process, in which methyl esters of carboxylic acids obtained by transesterification of oils from Brassicaceae are used as starting material, the organic phase is substantially composed of pelargonic acid and mono-methyl azelate, mono-methyl brassylate, methyl palmitate, methyl stearate, methyl dihydroxy stearate and methyl dihydroxy behenate, these latter in free form or esterified with pelargonic acid and/or mono-methyl azelate and mono-methyl brassylate.

In step c) of the process according to the invention, the organic phase obtained as oxidative cleavage product is fed to an apparatus (3) suitable to separate the saturated monocarboxylic acids from the derivatives of saturated carboxylic acids having more than one carboxylic function. Separation is advantageously performed by distillation processes in a rectification column. Distillation processes not subjecting the mixture obtained in step b) to high thermal stress, such as distillation in vapor current, thin film distillation, falling film distillation, molecular distillation, are preferred.

The single components of the residue from distillation can then be purified using conventional techniques. Before starting this purification process, the acids constituting the mixture of the products can be esterified.

In a preferred embodiment of the process in which esters of the unsaturated carboxylic acids are used as starting material, the monoesters of saturated carboxylic acids present in the residual organic phase can advantageously be hydrolyzed in alcohol and saturated carboxylic acids. The hydrolysis reaction can be performed using different techniques, such as only with water, with strong acid ion exchange resins or by catalyzing the reaction with enzymes.

In the case of hydrolysis with water, the reaction takes place at temperatures between 150 and 350° C., preferable between 180 and 320° C., at the corresponding vapor equilibrium pressure, with or without the addition of a catalyst and with a water/oil ratio preferably comprised between 0.5:1 and 5:1.

Hydrolysis with strong acid ion exchange resins is performed at the temperature of 100-140° C. Examples of suitable resins are those of the type Amberlyst® and Amberlite® (both produced by Rohm and Haas Co.).

In the case of reaction catalyzed by enzymes (lipases), it is advantageous to use lipases selected within the group comprising: *Candida cylindracea*, *Candida antarctica*, *Pseudomonas* sp., porcine pancreatic lipases, *Candida rugosa*, *Geotrichum candidum*, *Aspergillus niger*, *Mucor miehei*, *Rhizopus arrhizus*, *Rhizopus delemar*, *Rhizopus niveus*, *Chromobacterium viscosum*, *Thermomyces lanuginosus*, *Penicillium cyclopium*.

The hydrolysis reaction is advantageously performed at 100° C. continuously feeding an oil/water emulsion to one or more columns containing ion exchange acid resins. Said oil/water emulsion is obtained mixing the monoesters of saturated carboxylic acids present in the residual organic phase with water in an emulsifier, with an aqueous phase/organic phase weight ratio preferably comprised between 5:1 and 2:1, possibly in the presence of a surfactant to facilitate the emulsion between the two phases. Each column is advantageously provided with a fractionating column on the top, in order to separate methanol from water and to obtain a high purity methanol.

Following hydrolysis, an organic phase and an aqueous phase, possibly containing alcohol, are obtained. The organic phase principally contains saturated carboxylic acids with more than one acid function. Monocarboxylic acids, released following the hydrolysis reaction, diols and a reaction residue consisting of oligomers are also contained in the organic phase.

The carboxylic acids are advantageously separated from the diols and residue by distillation in a thin film evaporator.

The diols and the residue thus separated can be used, for example, as biofuel or recycled in the oxidative cleavage reactor (step b).

The evaporated carboxylic acids are then advantageously subjected to column distillation to separate the monocarboxylic acids with low molecular weight, thus purifying the saturated carboxylic acids having more than one acid function.

In a preferred embodiment of the process according to the invention, these carboxylic acids are further purified from the monocarboxylic acids with high molecular weight by means of extraction in water.

According to the type of derivatives of unsaturated carboxylic acids used as starting material, different saturated carboxylic acids having more than one acid function can be obtained, such as: oxalic acid, malonic acid, succinic acid, glutaric acid, adipic acid, pimelic acid, suberic acid, azelaic acid, sebacic acid, undecandicarboxylic acid, dodecandicarboxylic acid, brassylic acid, tetradecandicarboxylic acid, pentadecandicarboxylic acid. In a preferred embodiment of the process according to the invention, azelaic acid is principally obtained from the oxidative cleavage reaction of derivatives of oleic acid.

In another preferred embodiment of the process, brassylic acid is principally obtained from the oxidative cleavage reaction of derivatives of erucic acid.

The concentration (w/w) of hydrogen peroxide in the reaction mixture can be determined by techniques well-known in the art. The hydrogen peroxide concentration of Examples 1-3 is determined according to the method described in the patent application WO 02/063285.

EXAMPLE 1

Step a)

The following substances were fed continuously to a CSTR with a working capacity of 80 l, equipped with stirrer and with an adequate temperature regulation system:
methyl oleate (technical purity approximately 85%; flow rate 10 kg/h);
an aqueous solution of hydrogen peroxide at 60% (flow rate 2.3 kg/h);
tungstic acid ($H_2WO_4$) (flow rate 48 g/h).

The reaction was conducted at a constant temperature of 62° C. under vacuum (absolute pressure of 0.10-0.20*$10^5$ Pa) to evaporate the water fed together with the hydrogen peroxide; the evaporated gas was collected and condensed (approximately 1 kg/h of water).

Figure 3:
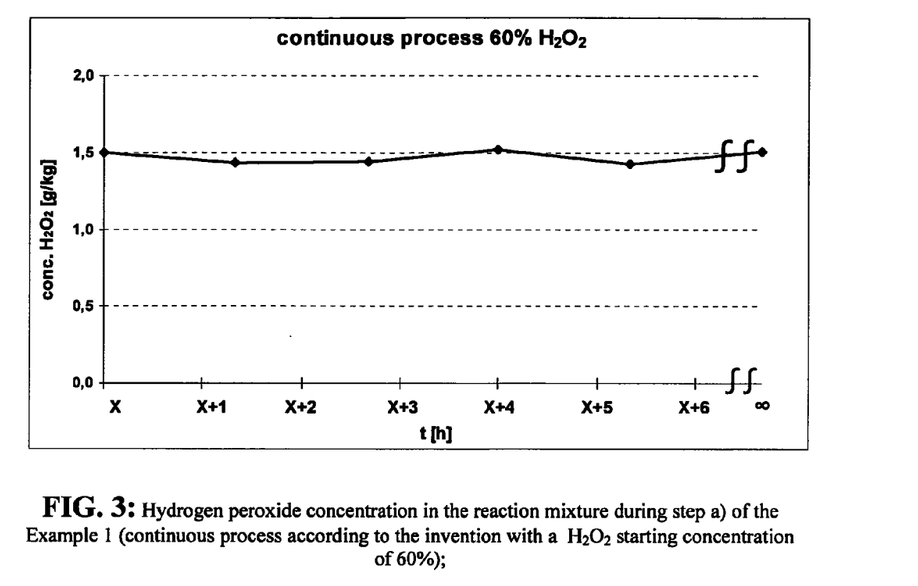
FIG. 3 is a diagram showing the hydrogen peroxide concentration in the reaction mixture during step a) of the Example 1 (continuous process according to the invention with a $H_2O_2$ starting concentration of 60%)

FIG. 3 shows the hydrogen peroxide over-all concentration during step a).

As can be seen in FIG. 3, the over-all hydrogen peroxide concentration in the reactor was constant at about 1.5 g/kg.

The intermediate product containing vicinal diols was continuously discharged from the reactor and fed to step b) by means of a gear pump, adjusted to maintain a constant level in the reactor, with a flow rate of approximately 11.4 kg.

Step b)

Step b) was performed in a jet loop reactor with a working capacity of 80 l equipped with a 3 $m^3$/h recirculation pump and heat exchanger. The intermediate product of step a) was continuously fed with a flow rate of 11.4 kg/h together with:
cobalt acetate ($Co(CH_3COOH)_2.4H_2O$), dissolved at 1.5% in an aqueous current (approximately 2 kg/h);
pressurized air (20*$10^5$ Pa; flow rate 12 to 15 kg/h).

The air flow rate was adjusted to maintain a constant $O_2$ content (approximately 10%) at the reactor outlet.

The reaction was conducted at 60° C., keeping constant the reaction volume to 50 l. The reaction time was about 3.5 h.

The reaction mixture of step b) was continuously discharged from the jet loop reactor and fed to a decanter to separate the oily phase from the aqueous phase. Approximately 13 kg/h of oily product was obtained.

Step (c)

The separated oily phase was dried and degassed, and then transferred to a distillation column which allowed fractioning of the monocarboxylic acids, to separate the pelargonic acid from the lighter monocarboxylic acids. The main component of the lighter monocarboxylic acids fraction (byproducts of the oxidative cleavage reaction) was octanoic acid.

Approximately 3.8 kg/h of vapor phase containing monocarboxylic acids (raw pelargonic acid), of which 3.5 kg/h are pelargonic acid with a titer of over 99%, was obtained. The 3.8 kg/h current of raw pelargonic acid contained approximately 3.3% of octanoic acid.

An organic current of approximately 9 kg/h, containing as major component mono-methyl azelate, together with methyl palmitate, methyl stearate and esters of methyl dihydroxy stearate, was extracted from the bottom of the distillation column.

Said organic current was then continuously fed to an emulsifier together with 18 kg/h of water. The emulsion was hydrolyzed by feeding it to three consecutive columns filled with acid ion exchange resin and heated at the temperature of 100° C. The total reaction time was 6 h.

Each column was provided with a fractionating column on the top, to separate 1.1 kg/h of methanol from water. Approximately 8.5 kg/h of carboxylic acids were obtained from the bottom of the column, of which about 4.3 kg was azelaic acid.

EXAMPLE 2 COMPARATIVE

Step a) Performed Batchwise vs Continuous with 60% $H_2O_2$

A batch process was performed placing in a 80 l reactor the following substances:
60 kg of methyl oleate (technical purity approximately 85%, the same used in Example 1),
300 g of tungstic acid (0.7% by moles with respect to the unsaturated fatty acid)
3 kg of 9,10-dihydroxymethyl stearate (intermediate obtained at the end of step (a) coming from a previous reaction, the so-called reaction activator).

The temperature was raised to 60-65° C. and 13.6 kg of 60% solution of $H_2O_2$ were added in 4 h.

During the reaction nitrogen was fluxed to distil a part of the water of the process and to prevent excessive dilution of $H_2O_2$.

Once the addition of $H_2O_2$ was completed, the reaction was continued at 65° C. for 3 h to obtain the intermediate product containing vicinal diols.

Figure 4:
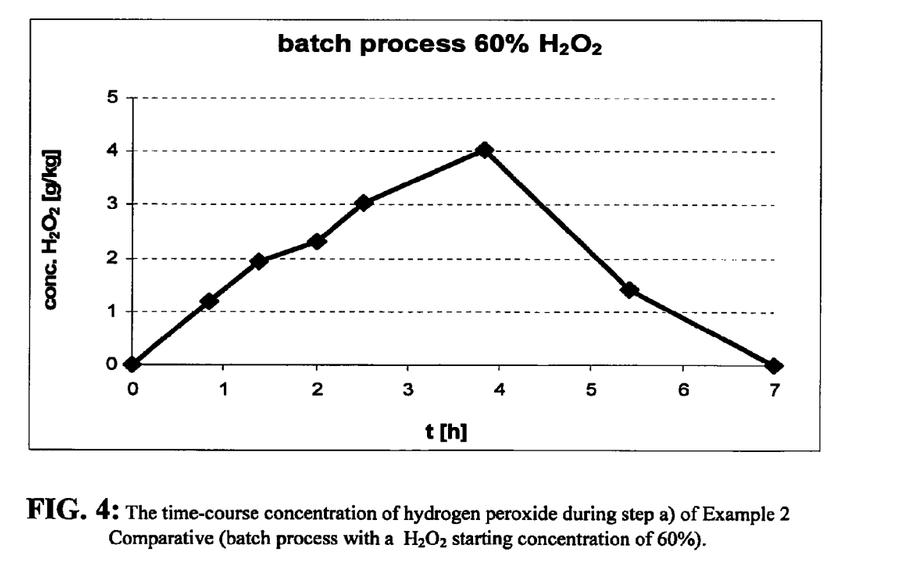
FIG. 4 is a diagram showing the time-course concentration of hydrogen peroxide during step a) of Example 2 Comparative (batch process with a $H_2O_2$ starting concentration of 60%)

FIG. 4 shows the time-course concentration of hydrogen peroxide during step a) of Example 2 Comparative. As can be seen in FIG. 4, the hydrogen peroxide concentration in the reaction mixture varied reaching peaks also two times higher than in Example 1 (FIG. 3).

In the continuous process according to Example 1 (FIG. 3), the concentration of $H_2O_2$ remained constant and on a significantly lower level leading to a safer process.

EXAMPLE 3 COMPARATIVE $H_2O_2$ Concentration Effect in Step a) Performed Batchwise Step a) of a batch process was performed according to Example 2 Comparative with the same total amount of $H_2O_2$ but with a lower starting concentration.

16.3 kg of 50% $H_2O_2$ solution were added in the same reactor in 4 h. Once the addition of $H_2O_2$ was completed, the reaction was continued at 65° C. for 4 h. Due to the lower starting concentration of hydrogen peroxide, a longer reaction time was required with respect to Example 2 Comparative.

Figure 5:
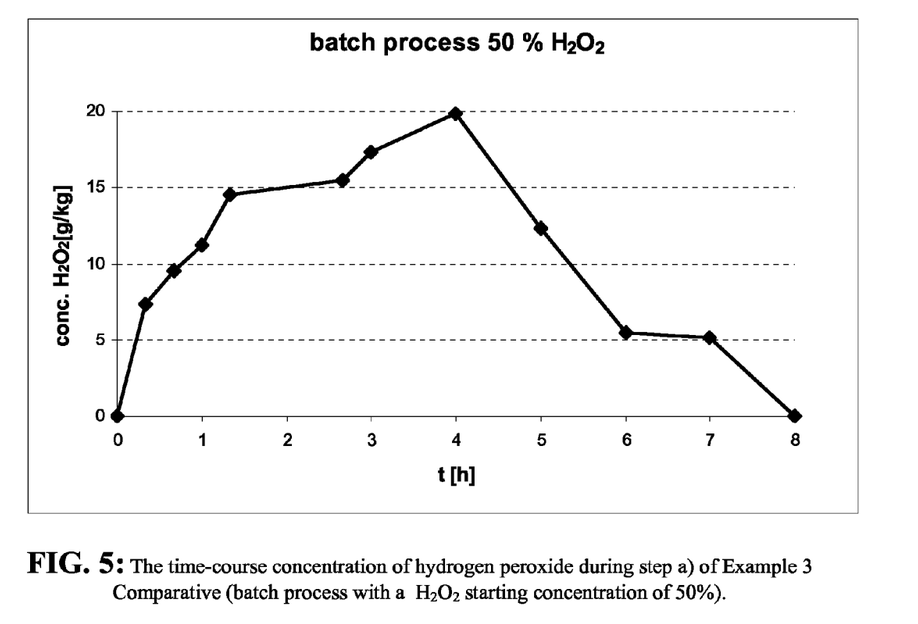
FIG. 5 is a diagram showing the time-course concentration of hydrogen peroxide during step a) of Example 3 Comparative (batch process with a $H_2O_2$ starting concentration of 50%).

FIG. 5 shows the time-course concentration of hydrogen peroxide during step a) of Example 3 Comparative. It can be noted that the hydrogen peroxide concentration was considerably higher than in Example 1 (FIG. 3), notwithstanding the $H_2O_2$ starting concentration being lower.

EXAMPLE 4 COMPARATIVE

Step b) Performed Batchwise vs Continuous 56 kg of the oily phase (intermediate product formed at the end of the reaction step (a) of Example 2 Comparative) were transferred to a jet loop reactor. 14 kg of aqueous solution of 1% cobalt acetate were added (0.4% by moles with respect to the diol produced in step (a)).

The reactor was then brought to 60-62° C. and to a pressure of $22*10^5$ Pa with air to perform step (b). Air was continuously fluxed to provide a sufficient supply of oxygen.

The batch reaction lasted 6 h.

At the end of step (b) hot separation of the aqueous phase from the organic phase was performed.

The separated organic phase was dried and degassed, and then transferred to a distillation column which allowed fractioning of the monocarboxylic acids, to separate the pelargonic acid from the lighter monocarboxylic acids (by-products of the oxidative cleavage reaction).

Approximately 16.8 kg of monocarboxylic acids (raw pelargonic acid), of which 14.4 kg was pelargonic acid with a titer of over 99% and approximately 1.5 kg was octanoic acid, were obtained.

The distillation residue contained approximately 19 kg of monomethyl azelate. The corresponding yield for the oxidative cleavage reaction (step b)) was of about 66% with respect to the moles theoretically obtainable.

The conversion achieved after 3.5 h reaction of step b) in the continuous process according to Example 1 was higher than the final yield reached after 6 h reaction in the batch process (Example 4 Comparative), as can be seen in Table 1:

TABLE 1

| Oxidative cleavage reaction yields (% moles of theoretical amount) | Example 1 | Example 4 Comparative |
| --- | --- | --- |
| Pelargonic acid | 77.3 | 65.1 |
| Azelaic acid | 79.8 | 67.2 |

The selectivity of the oxidative cleavage reaction in the in the continuous process according to Example 1 was also higher than in the batch process, as can be seen in Table 2, showing that the by-product/product ratio was lower.

TABLE 2

| By-product/product (% w/w) | Example 1 | Example 4 Comparative |
| --- | --- | --- |
| Octanoic acid/raw Pelargonic acid | 3.3 | 8.9 |

The invention claimed is:

1. A continuous process for the oxidative cleavage of derivatives of unsaturated carboxylic acids for the production of saturated carboxylic acids, which comprises the steps of:
   a) feeding to a first continuous reactor at least a derivative of an unsaturated carboxylic acid, an oxidizing compound and a catalyst capable of catalyzing the oxidation reaction of the olefinic double bond to obtain an intermediate compound containing vicinal diols;
   b) feeding to a second continuous reactor said intermediate compound, a compound containing oxygen and an aqueous phase comprising a catalyst capable of catalyzing the oxidation reaction of the vicinal diols to carboxylic groups, to obtain saturated monocarboxylic acids (i) and derivatives of saturated carboxylic acids with more than one acid function (ii), the output of this second continuous reactor comprising an aqueous phase and an organic phase;
   b') separating the aqueous phase from the organic phase of the product obtained as output from step b);
   c) transferring the organic phase of the product of step b) to an apparatus suitable to separate the saturated monocarboxylic acids (i) from the derivatives of carboxylic acids having more than one acid function (ii); and
   wherein in said steps a) and b the operations to feed reagents and to remove products take place simultaneously for the entire duration of the process, and in each of said step the process conditions remain substantially unchanged.

2. The continuous process according to claim 1, wherein the said step b') is performed by continuous centrifuging.

3. The continuous process according to claim 1, wherein the said step b') is performed by means of a disc separator.

4. The continuous process according to claim 1, wherein in step b') an organic solvent is added to improve the separation of the two phases.

5. The continuous process according to of claim 1, wherein the catalysts of steps a) and b) contained in the aqueous phase of step b') are recovered and recycled as catalysts of step b).

6. The continuous process according to claim 1, wherein the derivative of the unsaturated carboxylic acid is an ester comprising a C1-C9 alkyl group.

7. The continuous process according to claim 6, wherein said ester comprises an alkyl group which is methyl, ethyl or propyl.

8. The continuous process according to claim 6, wherein the ester is methyl oleate.

9. The continuous process according to claim 1, wherein said unsaturated carboxylic acids are present in vegetable oils belonging to the group of oils having a high content of monounsaturated acids such as soybean oil, olive oil, castor oil, sunflower oil, peanut oil, maize oil, palm oil, jatropha oil, cuphea oil, oils from Brassicaceae, *Lesquerella,* and mixtures thereof.

10. The continuous process according to claim 9, wherein the oil having a high content of monounsaturated acids is sunflower oil, oil from Brassicaceae and mixtures thereof.

11. The continuous process according to claim 1, wherein said unsaturated carboxylic acids belong to the group consisting of 9-tetradecenoic acid (myristoleic acid), 9-hexadecenoic acid (palmitoleic acid), 9-octadeceneoic acid (oleic acid), 12-hydroxy-9-octadeceneoic acid (ricinoleic acid), 9-eicosenoic acid (gadoleic acid), 13-docosenoic acid (erucic acid), 15-tetracosenoic acid (nervonic acid), 9,12-octadecadienoic acid (linoleic acid), and linolenic acid (9,12,15-octadecatrienoic acid).

12. The continuous process according to claim 11, wherein the unsaturated carboxylic acid is a monounsaturated carboxylic acid.

13. The continuous process according to claim 1, wherein the catalyst of step a) is used in a homogeneous or heterogeneous phase, optionally in a supported or nanostructured form, and belongs to the group of transition elements and acids, salts and complexes thereof.

14. The continuous process according to claim 13, wherein the catalyst of step a) is selected from the group of tungsten and molybdenum derivatives or mixtures thereof, said catalyst being present in a quantity between 0.03% and 3% by moles with respect to the total moles of unsaturations.

15. The continuous process according to claim 1, wherein the catalyst of step b) is used in a homogeneous or heterogeneous phase, and belongs to the group of transition elements and acids, salts and complexes thereof.

16. The continuous process according to claim 15, wherein the catalyst of step b) is selected from the group of the derivatives of cobalt or of manganese, including acetates, chlorides, sulphates, bromides and nitrates, said catalyst being present in a quantity between 0.05% and 3% by moles with respect to the diol.

17. The continuous process according to claim 1, wherein the oxidizing compound of step (a) is hydrogen peroxide present in aqueous solution at concentrations between 30 and 80%, the oxidizing compound of step (b) being air.

18. The continuous process according to claim 1, wherein step (a) is carried out at a pressure equal to or slightly lower than the atmospheric pressure, while step b) is carried out at a pressure higher than the atmospheric pressure.

19. The continuous process according to claim 1, wherein the reaction temperature of step a) and of step b) is comprised between 45 and 95° C.

20. The continuous process according to claim 1, wherein said step c) is carried out by distillation, preferably by thin layer distillation.

21. The continuous process according to claim 11, wherein the unsaturated carboxylic acid is 9-octadecenoic acid (oleic acid) or 13-docosenoic acid (erucic acid).

22. The continuous process according to claim 11, wherein the unsaturated carboxylic acid is 9-octadecenoic acid (oleic acid).

23. The continuous process according to claim 11, wherein the unsaturated carboxylic acid is 13-docosenoic acid (erucic acid).

* * * * *